US008805464B2

(12) United States Patent
Onoe et al.

(10) Patent No.: US 8,805,464 B2
(45) Date of Patent: Aug. 12, 2014

(54) BIO-INFORMATION MEASURING APPARATUS

(75) Inventors: Atsushi Onoe, Tsurugashima (JP); Yoshinori Kimura, Tsurugashima (JP)

(73) Assignee: Pioneer Corporation, Tokyo (JP)

( * ) Notice: Subject to any disclaimer, the term of this patent is extended or adjusted under 35 U.S.C. 154(b) by 1110 days.

(21) Appl. No.: 12/532,101

(22) PCT Filed: Mar. 20, 2007

(86) PCT No.: PCT/JP2007/055616
§ 371 (c)(1),
(2), (4) Date: Sep. 18, 2009

(87) PCT Pub. No.: WO2008/114401
PCT Pub. Date: Sep. 25, 2008

(65) Prior Publication Data
US 2010/0087717 A1 Apr. 8, 2010

(51) Int. Cl.
*A61B 5/1455* (2006.01)
(52) U.S. Cl.
USPC ......................................... 600/344
(58) Field of Classification Search
USPC .................... 600/310, 322, 323, 340, 344
See application file for complete search history.

(56) References Cited

U.S. PATENT DOCUMENTS

| | | | | |
|---|---|---|---|---|
| 4,865,038 A | * | 9/1989 | Rich et al. | 600/344 |
| 4,880,304 A | * | 11/1989 | Jaeb et al. | 600/328 |
| 5,224,478 A | * | 7/1993 | Sakai et al. | 600/335 |
| 5,638,818 A | | 6/1997 | Diab et al. | |
| 5,766,131 A | | 6/1998 | Kondo et al. | |
| 8,190,229 B2 | * | 5/2012 | Lowery et al. | 600/344 |

FOREIGN PATENT DOCUMENTS

| | | |
|---|---|---|
| JP | 09-038056 A | 2/1997 |
| JP | 10-509352 A | 9/1998 |
| JP | 2003-210425 A | 7/2003 |
| JP | 3490433 A | 1/2004 |
| WO | 96/13208 A1 | 5/1996 |

* cited by examiner

*Primary Examiner* — Eric Winakur
(74) *Attorney, Agent, or Firm* — Sughrue Mion, PLLC

(57) ABSTRACT

A bio-information measuring apparatus is provided, which suppresses pressure on a capillary vessel of body, stabilizes a measuring result of bio-information, and obtains a good S/N ratio.
In an bio-information measuring apparatus 1 in which a self-emission-type sensor device 10 for optically measuring bio-information of specimen 4 is attached to an attaching member 2, the attaching member 2 is composed of elastic material, and the attaching member 2 is arranged to be brought into contact with the specimen 4 at the time of measuring the bio-information.

5 Claims, 8 Drawing Sheets

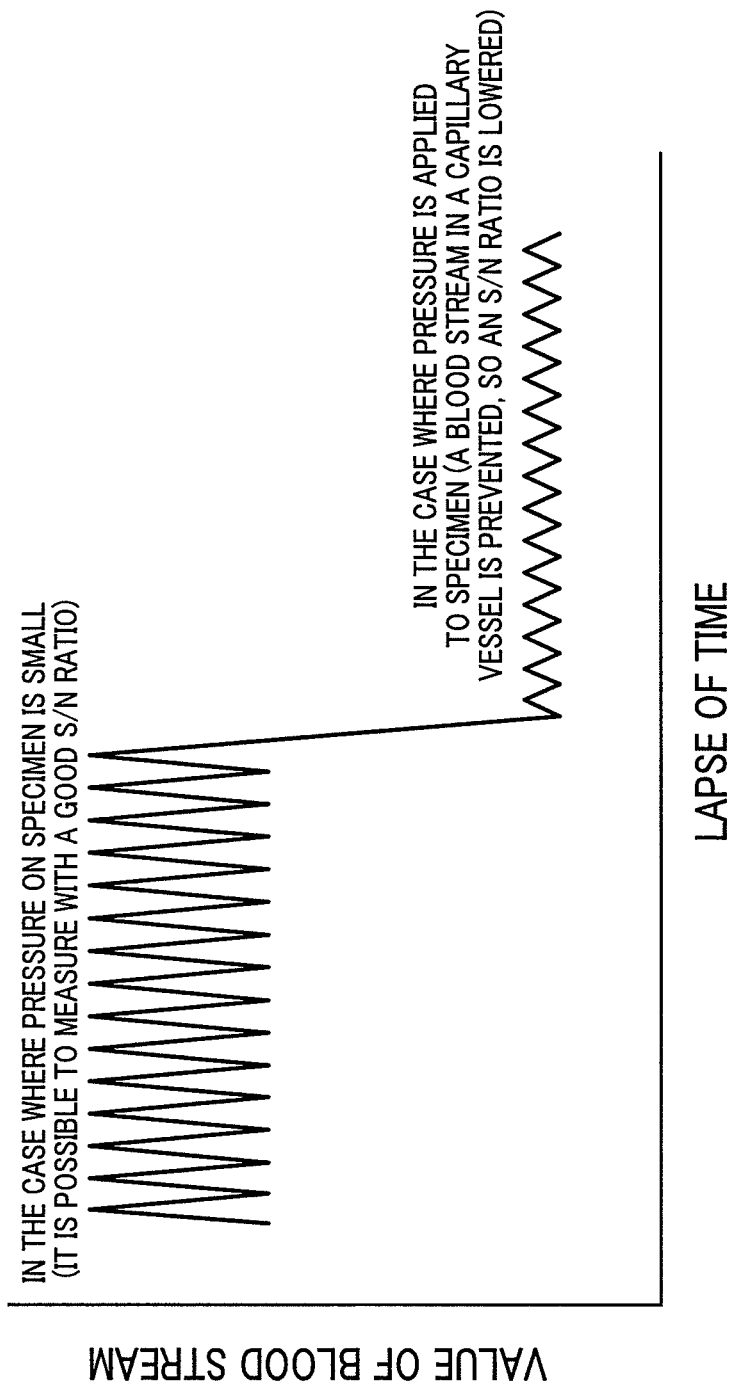

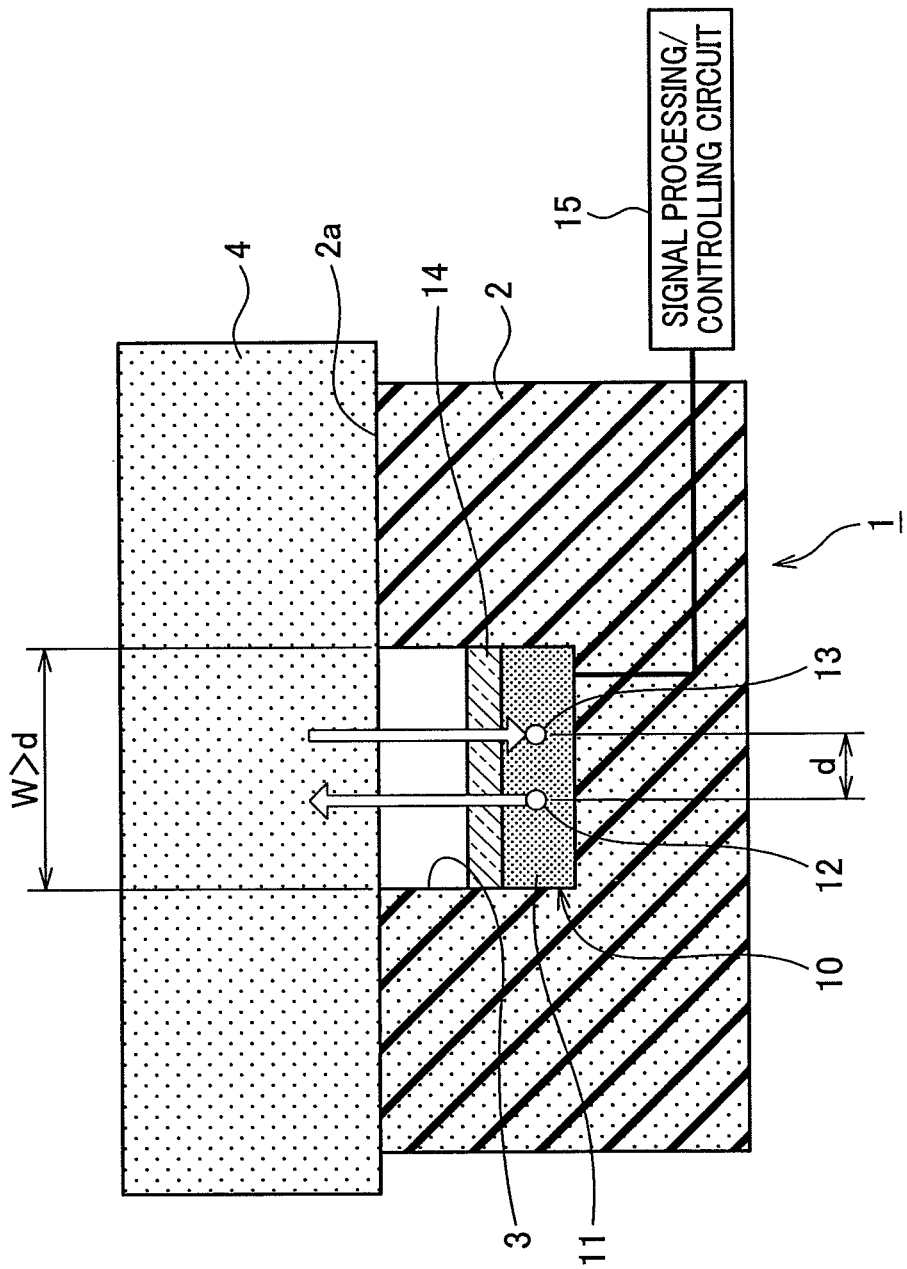

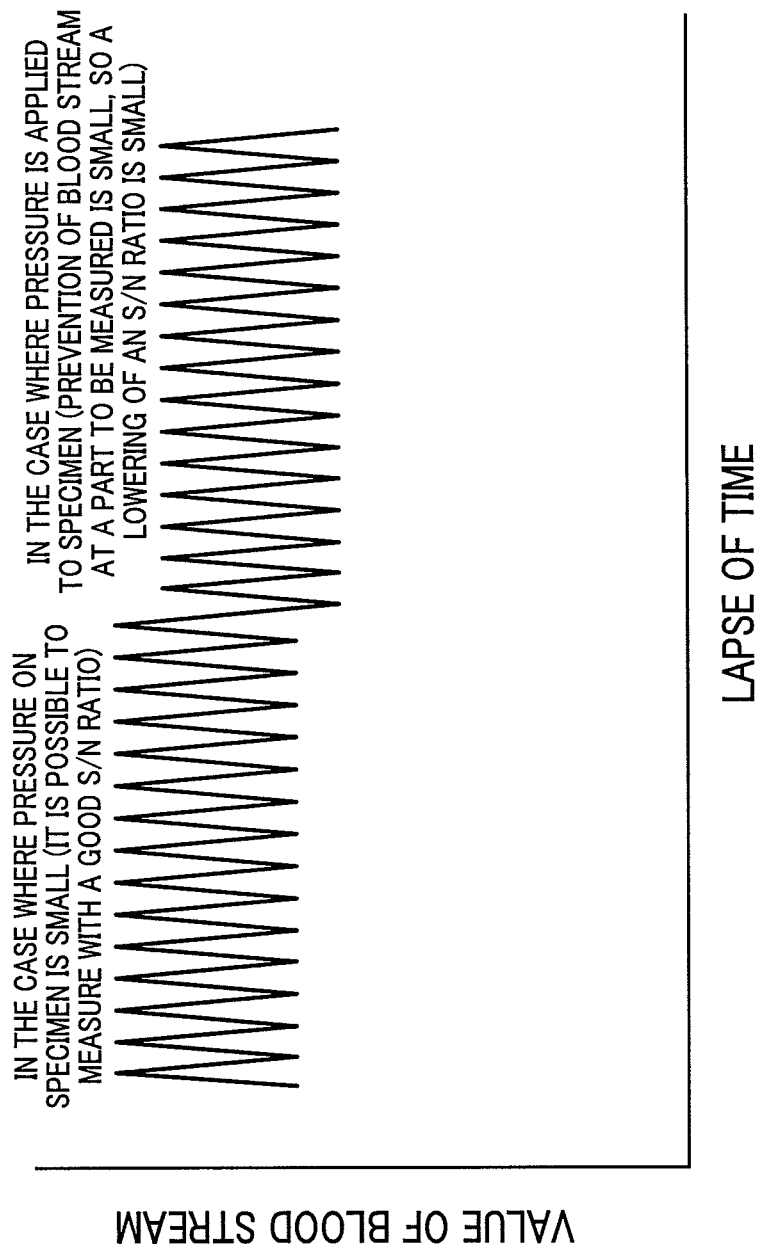

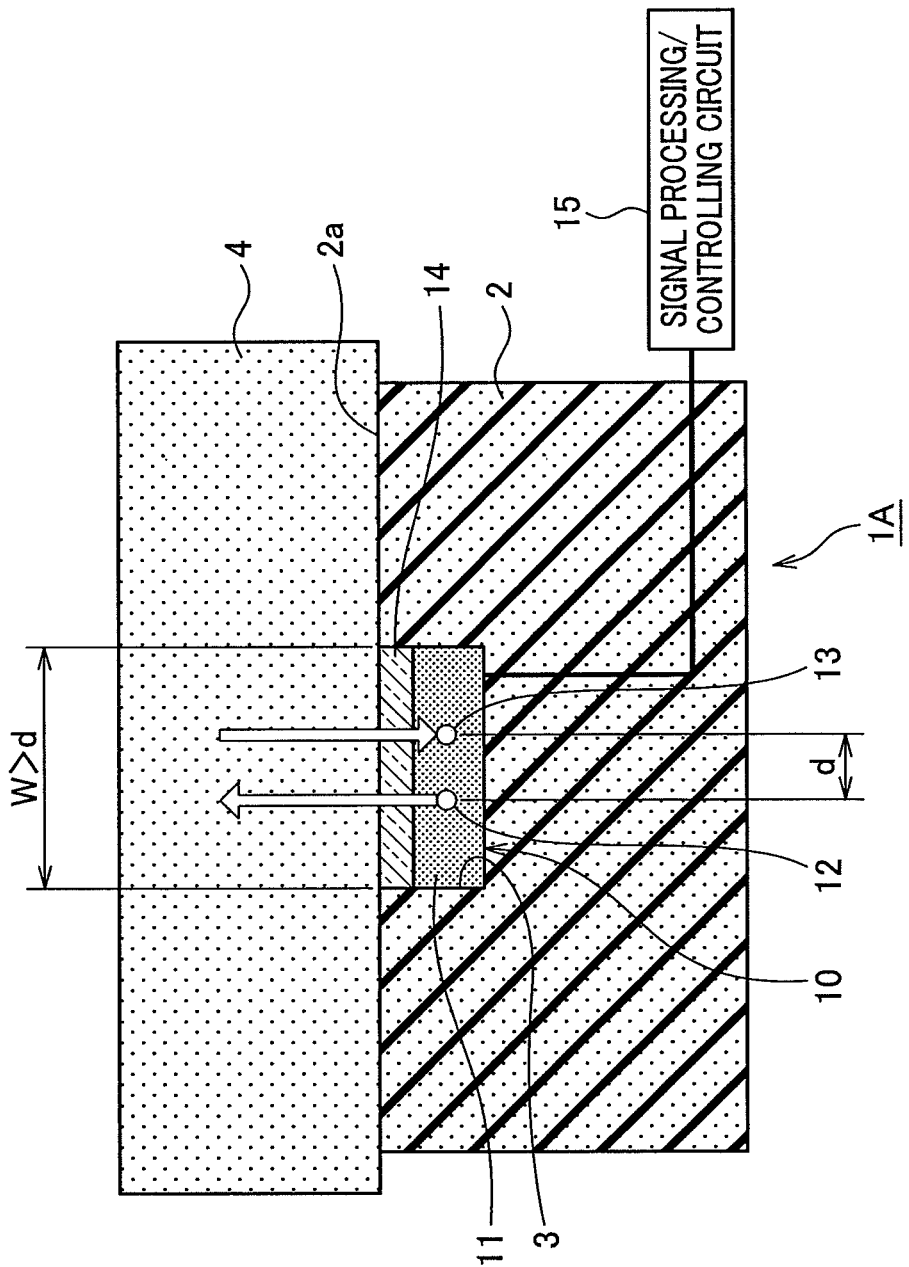

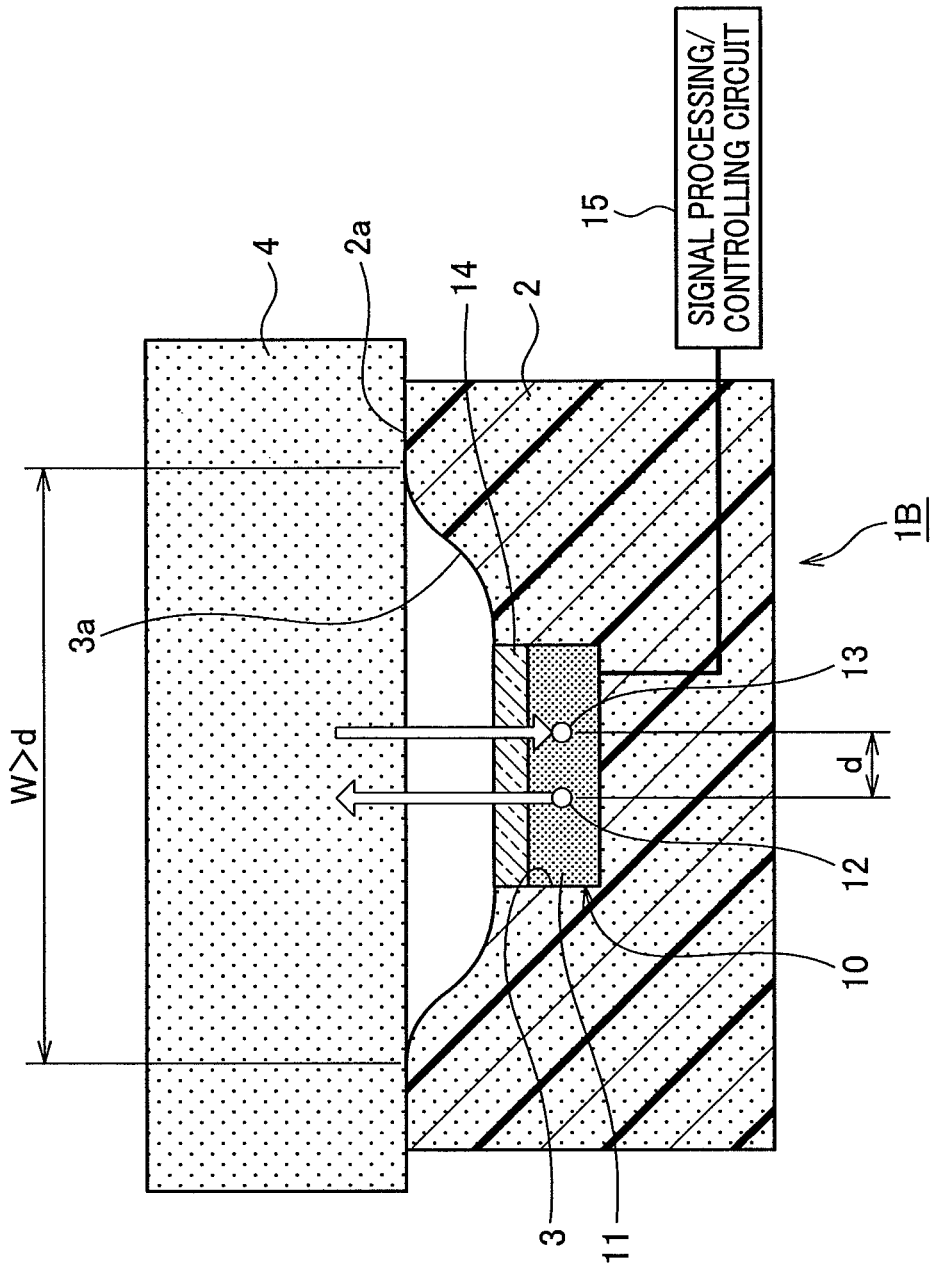

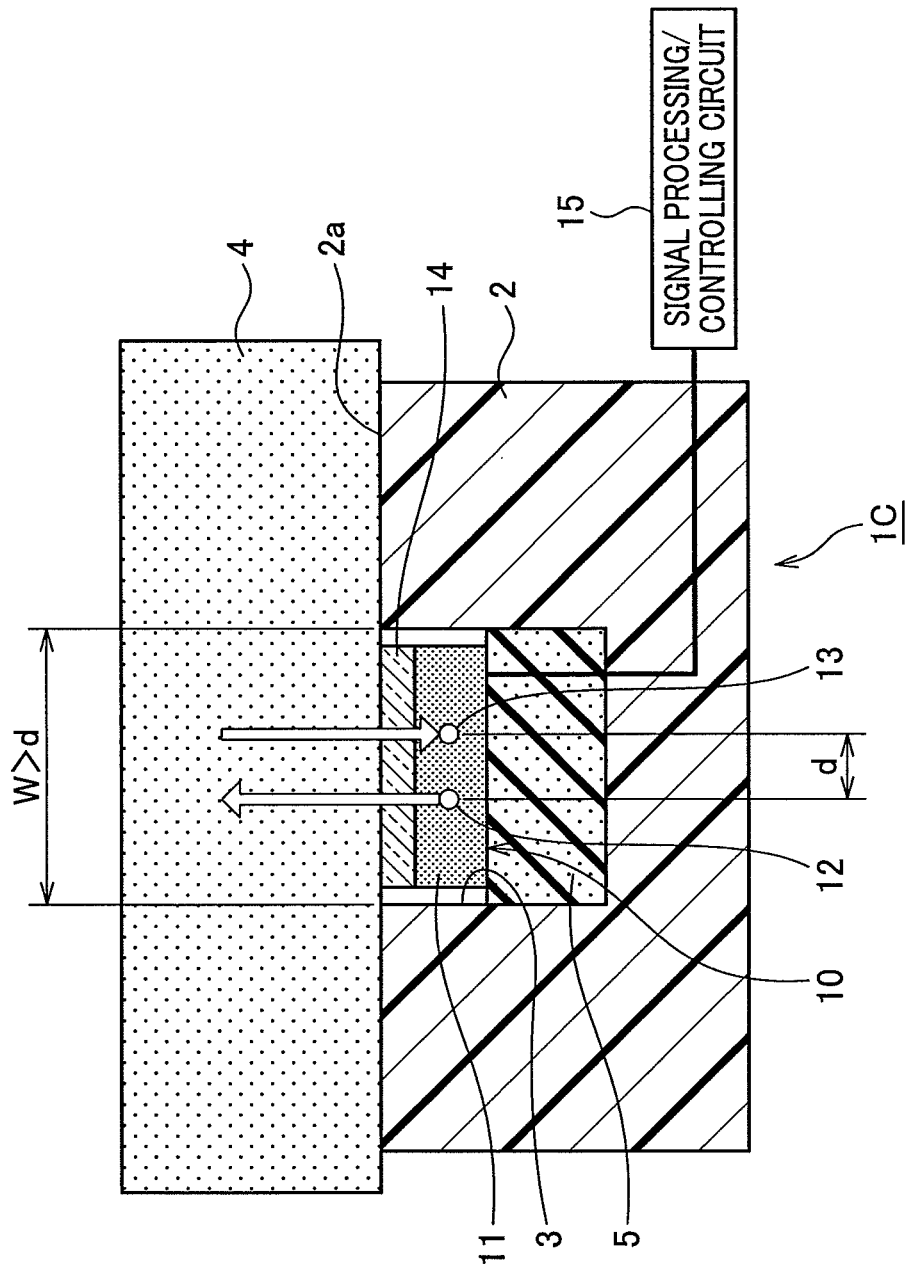

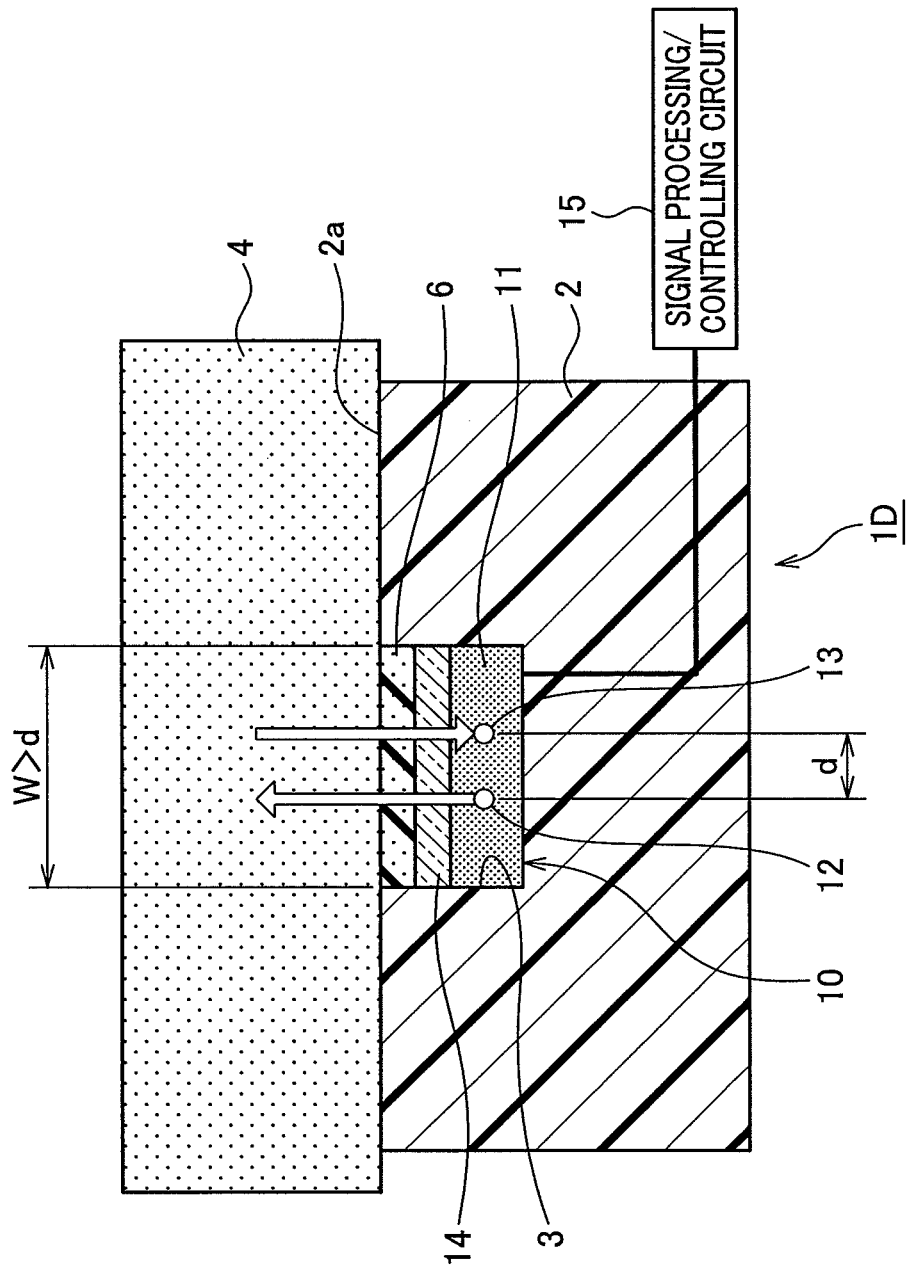

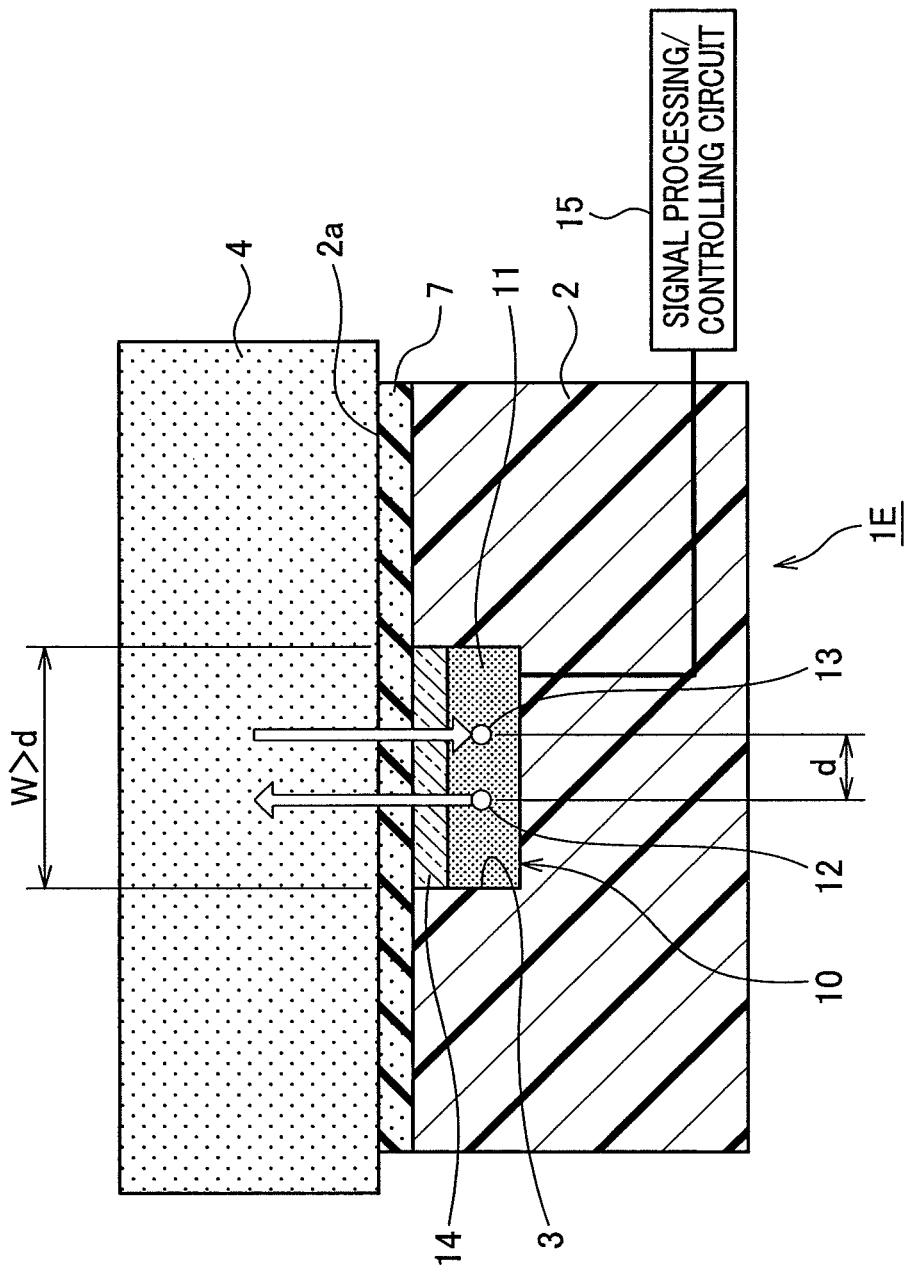

BIO-INFORMATION MEASURING APPARATUS

FIELD OF THE INVENTION

The present invention relates to a technical field of bio-information measuring apparatus for measuring bio-information, for example, a speed of blood stream, oxygen saturation, a beat of pulse, and so on of specimen.

BACKGROUND OF THE INVENTION

In the past, a bio-information monitoring system which includes a laser blood-stream measuring device for measuring a blood stream of specimen is disclosed in, for example, Patent Document 1. That is, this bio-information monitoring system includes a laser blood-stream measuring device for measuring a blood stream based on a scattered light caused by the fact that a laser light irradiated in an organization of body is scattered in the organization of body.

Specifically, this laser blood-stream measuring device includes a containing case which contains irradiating means for irradiating a laser light into a body, detecting means for detecting a scattered light caused by the fact that a laser light irradiated by the irradiating means is scattered in an organization of the body, and concentrating means for concentrating the scattered light and causing the detecting means to carry out detection. The outer surface of the containing case is structured in such a way that a contacting surface for contacting a surface of organization of body at the measuring time is formed into an approximate plane. Patent Document 1: Japanese Patent No. 3490433

DISCLOSURE OF THE INVENTION

Problems to be solved by the Invention

In a laser blood-stream measuring device of bio-information monitoring system disclosed in the above-mentioned Patent Document 1, skin of a finger or the like is pushed to a contacting surface of container case which has been formed into a plane, and the containing case is fixed by fixing means such as a band, and then, measuring is carried out. If skin of a finger or the like is successively pushed to the contacting surface, a capillary vessel is pressed. As a result, as shown in FIG. 1, a blood stream is prevented, and an SN ratio is lowered, so a good measuring is not carried out. Therefore, it is necessary to pay careful attention to a method of attaching a laser blood-stream measuring device.

On the other hand, an application of the laser blood-stream measuring device is thought such that the laser blood-stream measuring device is attached to a device such as a headphone, a headset, and bio-information of body is reflected in a operation of an entertainment device such as an audio player. Since a medical person does not attach a laser blood-stream measuring device, however, an attaching method of laser blood-stream device varies widely in the case of a structure of a conventional laser blood-stream measuring device, so it is not possible to analyze with a good SN ratio. This is a problem.

The present invention has been made in consideration of the above situation, and it is an example of an object of the invention to provide a bio-information measuring apparatus for suppressing pressure on a capillary vessel of body, stabilizing a measuring result of bio-information, and obtaining a good S/N ratio.

Means to Solve the Problems

In order to solve the above problem, the invention according to claim 1 relates to an bio-information measuring apparatus in which a self-emission-type sensor device for optically measuring bio-information of specimen is attached to an attaching member,
wherein the attaching member is composed of elastic material, and is brought into contact with the specimen at the time of measuring the bio-information.

In order to solve the above problem, the invention according to claim 5 relates to an bio-information measuring apparatus in which a self-emission-type sensor device for optically measuring bio-information of specimen is attached to an attaching member,
wherein a hollow is formed in the attaching member, an elastic member is contained in the hollow, and the self-emission-type sensor device is contained on an upper surface of the elastic member.

In order to solve the above problem, the invention according to claim 6 relates to an bio-information measuring apparatus in which a self-emission-type sensor device for optically measuring bio-information of specimen is attached to an attaching member,
wherein a hollow is formed in the attaching member, the self-emission-type sensor device is contained in the hollow, and an elastic member of permeability is mounted on at least an upper surface of self-emission-type sensor device.

BRIEF DESCRIPTION OF THE DRAWINGS

FIG. 1 is a view showing a waveform of blood stream obtained by a conventional laser blood-stream measuring apparatus.

FIG. 2 is a schematic sectional view showing a bio-information measuring apparatus according to the first embodiment of the present invention.

FIG. 3 is a view showing a waveform of blood stream obtained by a bio-information measuring apparatus according to the first embodiment of the present invention.

FIG. 4 is a schematic sectional view showing a bio-information measuring apparatus according to the second embodiment of the present invention.

FIG. 5 is a schematic sectional view showing a bio-information measuring apparatus according to the third embodiment of the present invention.

FIG. 6 is a schematic sectional view showing a bio-information measuring apparatus according to the fourth embodiment of the present invention.

FIG. 7 is a schematic sectional view showing a bio-information measuring apparatus according to the fifth embodiment of the present invention.

FIG. 8 is a schematic sectional view showing a bio-information measuring apparatus according to the sixth embodiment of the present invention.

EXPLANATION OF REFERENCE NUMERALS 1 bio-information measuring apparatus
2 containing member
3 hollow
4 specimen
5 elastic member
6 elastic plate
7 elastic plate
10 self-emission-type sensor device
11 substrate
12 laser diode
13 photo-diode
14 front surface plate
15 signal processing/controlling circuit

PREFERRED EMBODIMENTS FOR CARRYING OUT THE INVENTION

Now, the preferred embodiments of the present invention will be described with reference to the accompanying drawings. The first to sixth embodiments which will be described below are embodiments in which the present invention is applied to a medical care as an example of a self-emission-type sensor device.

(First Embodiment)

Referring to FIG. 2, a bio-information measuring apparatus according to the first embodiment of the present invention will be described.

As shown in FIG. 2, a bio-information measuring apparatus 1 includes a containing member 2 made of soft elastic material such as sponge, or a spring (in the present embodiment, sponge is used) as an example of an attaching member, and an upper surface of the containing member 2 is a contacting surface 2a with a body of specimen 4. A hollow 3 with a rectangular shape in a plane is formed in the containing member 2. In the hollow 3, a self-emission-type sensor device 10 which optically measures bio-information of the specimen 4 is contained. As the self-emission-type sensor device 10 according to the present embodiment, for example, a micro-sensor is used.

The self-emission-type sensor device 10 includes a substrate 11 as an example of a holding member, a laser diode 12 disposed in the substrate 11 as an example of an irradiating unit for irradiating a laser light onto the specimen 4, a photo-diode 13 disposed in the substrate 11 as an example of a light-receiving unit for detecting a scattered light from the specimen 4 caused by the irradiated laser light, and a front surface plate 14 of permeability disposed in front of the laser diode 12 and the photo-diode 13 and in an opposed relationship with the specimen 4. The laser diode 12 is arranged to irradiate light, and the photo-diode 13 is arranged to receive light, through the front surface plate 14.

Here, as a semi-conductor laser of the laser diode 12, in the most cases, for example, a laser of fabri-pellow (FP) type which is relatively inexpensive, or a surface-emission laser is used. Although the laser diode 12 and the photo-diode 13 are arranged to be disposed in the substrate 11, a member is not limited to the substrate 11, but any member will be available, as long as such member holds the laser diode 12 and the photo-diode 13. In the case where the above EP-type laser is used, since light is irradiated from an end surface, it is possible to irradiate light onto a body by utilizing a slope and the like (not shown) of the laser containing unit as a reflecting surface. The fact that light irradiated from the laser diode 12 directly impinges on the photo-diode 13 not through a body prevents the detection of bio-information which is an original purpose. Therefore, it is preferable to provide a light shield wall (not shown) between the laser diode 12 and the photo-diode 13. As material used for the light-shield wall, a reflecting film, resin, or the like through which a laser light is not transmitted is desirable.

Further, the front surface plate 14 has a function of protecting optical parts such as the laser diode 12, and the photo-diode 13. In the case where light irradiated from the laser diode 12 is a visible light, a glass plate is used, and in the case of an infrared light, a silicon plate is used. On the front surface plate 14 above the photo-diode 13, a light-shield film (not shown) is formed, to restrict light incident on the photo-diode 13. Thus, only light from the upper to the lower in FIG. 2 is incident on the photo-diode 13. Therefore, light which should not be detected is prevented from incidence on the photo-diode 13, so the accuracy of detection is improved. As a structure which produces the same effects, for example, a very small pinhole is formed in the front surface plate 14, and the very small pinhole and the above light-shield film are combined with each other, so light which should not be detected is surely prevented from incidence on the photo-diode 13.

In the self-emission-type sensor device 10, the laser diode 12 irradiates a laser light onto skin of body of the specimen 4, the laser light is scattered by an organization of body such as a red blood cell under the skin, and a scattered light returned after such scattering is received by the photo-diode 13, so a speed of blood stream, oxygen saturation, and another ingredient of body fluid are measured. The self-emission-type sensor device 10 is electrically connected to a signal processing/controlling circuit 15, a power supply not shown, and the like, and the signal processing/controlling circuit 15 has a function of amplifying a scattered light received by the self-emission-type sensor device 10, and analyzing the scattered light to obtain a speed of blood stream or the like. A portion or the whole of the signal processing/controlling circuit 15 or the like may be inserted in the substrate 11. In this case, silicone is used as the substrate, and an integrated circuit is fabricated on this silicone substrate 11, so the self-emission-type sensor device 10 can become small in size.

Assuming that a distance between the center of the laser diode 12 and the center of the photo-diode 13 is d, the hollow 3 formed in the containing member 2 is set in such a way that a minimum width D of aperture thereof is a width which encompasses at least the laser diode 12 and the photo-diode 13. That is, assuming that a minimum aperture width D of aperture portion of the hollow 3 as seen from the upper is W, W is greater than d.

Here, the distance d between the center of the laser diode 12 and the center of the photo-diode 13 is set, based on the conditions that a scattered light received by the photo-diode 13 based on a laser light irradiated from the laser diode 12 is not prevented, and based on the conditions that miniaturization of the self-emission-type sensor device 10 can be maintained.

Although the containing member 2 appears to be a member which contains the self-emission-type sensor device 10 in the drawings, the containing member 2 may be a portion of product in which the self-emission-type sensor device 10 is inserted and utilized, for example. Although sponge is used as an example of material of the containing member 2, the containing member 2 may be another soft elastic material which constitutes a product itself, provided that the self-emission-type sensor device 10 can be inserted in the product in the present embodiment.

Now, the operation and the effect of the present embodiment will be explained.

As shown in FIG. 2, in a bio-information measuring apparatus 1 according to the present embodiment, for example, a tip of finger which is the specimen 4 is brought into contact with a contacting surface 2a across an aperture of the hollow 3 of the containing member 2 in which the self-emission-type sensor device 10 is inserted. At this time, since the containing member 2 is formed with a soft elastic material, the containing member 2 is resiliently deformed, and a pressure on a tip of finger which is the specimen 4 is small.

Subsequently, when the laser diode 12 is driven, a laser light is irradiated from the laser diode 12, the laser light passes through the front surface plate 14, and is irradiated onto a tip of finger which is the specimen 4, so a speed of blood stream of organization of body is measured. At this time, it is desirable that apart onto which a laser light is irradiated is a part which is relatively close to an epidermo of skin, and in which capillary vessels are densely distributed (for example, a hand, a leg, a face, an ear, and so on).

A laser light irradiated onto a tip of finger which is the specimen 4 penetrates up to a certain depth of body, and is scattered by an organization of body such as blood, a cell of skin of the specimen. This scattered light is concentrated by concentrating means such as a lens (not shown), and is detected by the photo-diode 13. Here, a Doppler-shift is caused in light scattered by a red blood cell flowing in a blood vessel, and a wavelength of light varies in accordance with a moving speed of red blood cell, i.e., a streaming speed of blood. By detecting an amount of Doppler-shift, a speed of blood stream can be calculated.

Further, the photo-diode 13 receives a scattered light from an organization of body, and it is possible to obtain bio-information such as an amount of blood stream, an amount of blood stream, a beat of pulse, in addition to a speed of blood stream in an organization of body.

Thus, in accordance with the present embodiment, since the specimen 4 is brought into contact with the attaching member 2 made of elastic material at the time of measuring bio-information, a pressure applied to the specimen 4 by the attaching member 2 becomes small, and a pressure on a capillary vessel of body which is the specimen 4 is suppressed, at the time of measuring bio-information of the specimen 4. As shown in FIG. 3, a measuring result of bio-information is stabilized, and a good S/N ratio can be obtained.

Further, according to the present embodiment, since the specimen 4 is brought into contact with a contacting surface 2a across an aperture of the hollow 3 of the containing member 2, a pressure on the specimen 4 becomes further small. Therefore, as shown in FIG. 3, in the case where a pressure on the specimen 4 which is a part to be measured is small, it is possible to measure with a good S/N ration. Further, it is recognized that even if the specimen 4 which is a part to be measured is pressed, a blocking of blood stream at a part to be measured is small, and the reduction of S/N ration is slight.

Further, according to the present embodiment, the hollow 3 with a rectangular shape in a plane is formed in the containing member 2, and the self-emission-type sensor device 10 is contained in the hollow 3. Therefore, the self-emission-type sensor device 10 can be surely and easily positioned at a non-contacting part relative to the specimen 4.

Although light from the specimen 4 caused by an irradiated light is a scattered light in the present embodiment, the light may be a reflected light, a diffracted light, a refracted light, a transmitted light, a Doppler-shifted light, and so on.

Although the hollow 3 is a rectangular shape in a plane in the present embodiment, the hollow 3 may be a polygon, a circle, an ellipse, a semi-circle in a plane. This is similar in the following embodiments in which the hollow 3 is formed.

Further, although the whole of the containing member 2 is composed of sponge in the present embodiment, the containing member 2 is not limited thereto, the containing member 2 may be composed of, for example, cushion material in which a soft material body of synthetic resin film or the like is filled with liquid or gel material. With this arrangement, as compared with the above-mentioned sponge, the containing member 2 can be brought into close contact with a surface of body which is the specimen 4, and a pressure on a surface of body can be effectively relieved. From such condition, it is desirable that the hardness of soft elastic material in the present invention is lower than the hardness of surface of body which is the specimen 4. This is similar for soft elastic material in the embodiments mentioned below.

In the present embodiment, in the case of a medical use, if the hollow 3 is filled with a clear liquid, an interface between the self-emission-type sensor device 10 and skin of the specimen 4 can be maintained in a stable condition, and it is possible to measure a body in a remarkably stable condition.

(Second Embodiment)

FIG. 4 is a schematic sectional view showing a bio-information measuring apparatus according to the second embodiment of the present invention. With the same characters used for the same or corresponding parts as in the above-mentioned first embodiment, an explanation of the second embodiment will be made. The same characters are also used in the other embodiments.

As shown in FIG. 4, a bio-information measuring apparatus according to the present embodiment includes a containing member 2 as an attaching member which is made of soft elastic material, and the containing member 2 is formed with a hollow 3 with a rectangular shape in a plane. A self-emission-type sensor device 10 which optically measures bio-information of the specimen 4 is contained in the hollows 3. In the present embodiment, the self-emission-type sensor device 10 is contained in such a way that an upper surface of the self-emission-type sensor device 10, i.e., an upper surface of a front surface plate 14 is slightly lower than a contacting surface 2a of the attaching member 2 with the specimen 4.

The self-emission-type sensor device 10 includes a substrate 11 as an example of a holding member, a laser diode 12 disposed in the substrate 11 as an example of an irradiating unit for irradiating a laser light onto the specimen 4, a photo-diode 13 disposed in the substrate 11 as an example of a light-receiving unit for detecting a scattered light from the specimen 4 caused by the irradiated laser light, and a front surface plate 14 of permeability disposed in front of the laser diode 12 and the photo-diode 13 and in an opposed relationship with the specimen 4. The laser diode 12 is arranged to irradiate light, and the photo-diode 13 is arranged to receive light, through the front surface plate 14. Since the other structure and operation of the self-emission-type sensor device 10 are the same as in the above-mentioned first embodiment, an explanation thereof will be omitted. This is the same in a self-emission-type sensor device 10 in the embodiments mentioned below.

Assuming that a distance between the center of the laser diode 12 and the center of the photo-diode 13 is d, the hollow 3 formed in the containing member 2 is set in such a way that a minimum width D of aperture thereof is a width which encompasses at least the laser diode 12 and the photo-diode 13. That is, assuming that a minimum aperture width of aperture portion of the hollow 3 as seen from the upper is W, W is greater than d. This is the same in the relationship between the hollow 3 and a distance d between the center of the laser diode 12 and the center of the photo-diode 13 in the embodiments mentioned below.

Thus, in accordance with the present embodiment, the attaching member 2 is composed of soft elastic material, and the self-emission-type sensor device 10 is contained in the hollow 3 in such a way that an upper surface of the front surface plate 14 of the self-emission-type sensor device 10 is slightly lower than a contacting surface 2a of the attaching member 2 with the specimen 4. Therefore, at the time of measuring bio-information of the specimen 4, a capillary vessel of body which is the specimen 4 is not unnecessarily pressed, a measuring result of bio-information is stabilized, and a good S/N ratio can be obtained.

Further, in accordance with the present embodiment, the self-emission-type sensor device 10 is contained in the hollow 3 in such a way that an upper surface of the front surface plate 14 of the self-emission-type sensor device 10 is slightly lower than a contacting surface 2a of the attaching member 2 with the specimen 4. Therefore, it is possible to prevent, in advance, piling-up of impurities such as dust.

(Third Embodiment)

FIG. 5 is a schematic sectional view showing a bio-information measuring apparatus according to the third embodiment of the present invention.

As shown in FIG. 5, a bio-information measuring apparatus 1B according to the present embodiment includes a containing member 2, as an attaching member, made of soft elastic material, and a hollow 3 is formed in the containing member 2. A self-emission-type sensor device 10 which optically measures bio-information of the specimen 4 is contained in the hollow 3.

In the present embodiment, a gently slanted slope 3a is formed at an edge of aperture of the hollow 3. The slope 3a is formed in such away that the slope 3a is gently slanted in a curved condition, from a contacting surface 2a of the containing member 2 with the specimen 14, up to an upper surface of the front surface plate 14 of the self-emission-type sensor device 10.

Thus, in accordance with the present embodiment, the attaching member 2 is composed of soft elastic material, and a gently slanted slope 3a is formed at an edge of aperture of the hollow 3. Therefore, at the time of measuring bio-information of the specimen 4, similarly with the above-mentioned first embodiment, a pressure on the specimen 4 by the attaching member 2 becomes small, an pressure on a capillary vessel of body of the specimen 4 is suppressed. As shown in FIG. 3, a measuring result of bio-information is stabilized, and it is possible to obtain a good S/N ration.

Further, in accordance with the present embodiment, a gently slanted slope 3a is formed at an edge of aperture of the hollow 3. Therefore, similarly with the second embodiment, it is possible to prevent, in advance, piling-up of impurities such as dust in the hollow 3.

Further, in the present embodiment, in the case of a medical use, similarly with the first embodiment, if the hollow 3 is filled with a clear liquid, an interface between the self-emission-type sensor device 10 and skin of the specimen 4 can be maintained in a stable condition, and it is possible to measure a body in a remarkably stable condition.

(Fourth Embodiment)

FIG. 6 is a schematic sectional view showing a bio-information measuring apparatus according to the fourth embodiment of the present invention.

As shown in FIG. 6, a bio-information measuring apparatus 1C according to the present embodiment includes a containing member 2, as an attaching member, formed with synthetic resin such as silicon resin, and a hollow 3 is formed in the containing member 2. A soft elastic member 5 made of sponge, a spring, or the like (in the present embodiment, sponge is used) is contained in the hollow 3. A self-emission-type sensor device 10 which optically measures bio-information of the specimen 4 is contained on an upper surface of the elastic member 5.

The self-emission-type sensor device 10 is located apart from the attaching member 2 by a space 2b, and is supported by the elastic member 5, so that it can be moved lengthwise and crosswise. Here, a distance of the space 2b formed between the self-emission-type sensor device 10 and the attaching member 2 is set in such a way that the self-emission-type sensor device 10 can be moved lengthwise and crosswise.

Therefore, in a bio-information measuring apparatus 1C according to the present embodiment, for example, a tip of finger which is the specimen 4 is brought into contact with an upper surface of the front surface plate 14 of the self-emission-type sensor device 10 and the contact surface 2a of the containing member 2. At this time, since the self-emission-type sensor device 10 is supported by the elastic member 5 of soft material, the elastic member 5 is resiliently deformed, so a pressure applied to a tip of finger which is the specimen 4 is small.

Subsequently, when the laser diode 12 is driven, a laser light is irradiated from the laser diode 12, the laser light passes through the front surface plate 14, and is irradiated onto a tip of finger which is the specimen 4, so a speed of blood stream of organization of body is measured, for example.

Thus, in accordance with the present embodiment, the elastic member 5 is contained in the hollow 3, and the self-emission-type sensor device 10 is contained on an upper surface of the elastic member 5, so the self-emission-type sensor device 10 can be moved lengthwise and crosswise. Therefore, at the time of measuring bio-information of the specimen 4, a pressure applied to the specimen 4 by the self-emission-type sensor device 10 becomes small, and an pressure on a capillary vessel of body which is the specimen 4 is suppressed. As shown in FIG. 3, a measuring result of bio-information is stabilized, and it is possible to obtain a good S/N ration.

(Fifth Embodiment)

FIG. 7 is a schematic sectional view showing a bio-information measuring apparatus according to the fifth embodiment of the present invention.

As shown in FIG. 7, a bio-information measuring apparatus 1D according to the present embodiment includes a containing member 2, as an attaching member, formed with synthetic resin such as silicon resin, and a hollow 3 with a rectangular shape in a plane is formed in the containing member 2. A self-emission-type sensor device 10 which optically measures bio-information of the specimen 4 is contained in the hollow 3. An elastic plate 6 as an elastic member of permeability, which is formed into a plate, is contained on an upper surface of the front surface plate 14 of the self-emission-type sensor device 10. The elastic plate 6 is composed of soft material such as sponge.

Further, in the present embodiment, the self-emission-type sensor device 10 and the elastic plate 6 are contained in such a way that an upper surface of the elastic plate 6 is slightly lower than a contacting surface 2a of the attaching member 2 with the specimen 4.

Therefore, in a bio-information measuring apparatus 1D according to the present embodiment, for example, a tip of finger which is the specimen 4 is brought into contact with an upper surface of the elastic plate 6 and the contact surface 2a of the containing member 2. At this time, the elastic plate 6 is resiliently deformed, so a pressure applied to a tip of finger which is the specimen 4 is small.

Subsequently, when the laser diode 12 is driven, a laser light is irradiated from the laser diode 12, the laser light passes through the front surface plate 14 and the elastic plate 6, and is irradiated onto a tip of finger which is the specimen 4, and therefore, for example, a speed of blood stream of organization of body is measured.

Thus, in accordance with the present embodiment, the hollow 3 is formed in the attaching member 2, the self-emission-type sensor device 10 is contained in the hollow 3, and the elastic plate 6 of permeability is contained on an upper surface side of the self-emission-type sensor device 10. Therefore, at the time of measuring bio-information of the specimen 4, a pressure applied to the specimen by the elastic member 6 becomes small, a pressure on a capillary vessel of body which is the specimen 4 is suppressed, similarly with the above-mentioned first embodiment, and a measuring result of bio-information is stabilized, and it is possible to obtain a good S/N ration.

Further, in accordance with the present embodiment, the self-emission-type sensor device 10 and the elastic plate 6 are contained in the hollow 3 in such a way that an upper surface of the elastic plate 6 of the self-emission-type sensor device 10 is slightly lower than a contacting surface of the attaching member 2 with the specimen 4. Therefore, it is possible to prevent, in advance, piling-up of impurities such as dust.

(Sixth Embodiment)

FIG. 8 is a schematic sectional view showing a bio-information measuring apparatus according to the sixth embodiment of the present invention.

As shown in FIG. 8, a bio-information measuring apparatus 1E according to the present embodiment includes a containing member 2, as an attaching member, formed with synthetic resin such as silicon resin, and a hollow 3 is formed in the containing member 2. A self-emission-type sensor device 10 which optically measures bio-information of the specimen 4 is contained in the hollow 3. Here, the self-emission-type sensor device 10 is contained in the hollow 3 in such a way that an upper surface of the front surface plate 14 of the self-emission-type sensor device 10 is in the same level as a contacting surface 2a of the attaching member 2 with specimen 4.

Therefore, in the present embodiment, an elastic plate 7 as an elastic member of permeability which is composed of soft material and which is formed into a plate is attached to the an upper surface of the self-emission-type sensor device 10, i.e., an upper surface of the front surface plate 14, and a contacting surface 2a of the attaching member 2 in such a way that the elastic plate 7 covers the upper surface of the front surface plate 14, and the contacting surface 2a of the attaching member 2.

Therefore, in a bio-information measuring apparatus 1E according to the present embodiment, for example, the whole tip of finger which is the specimen 4 is brought into contact with an upper surface of the elastic plate 7. At this time, the elastic plate 7 is resiliently deformed, so a pressure applied to a tip of finger which is the specimen 4 is small.

Subsequently, when the laser diode 12 is driven, a laser light is irradiated from the laser diode 12, the laser light passes through the front surface plate 14 and the elastic plate 7, and is irradiated onto a tip of finger which is the specimen 4, and therefore, for example, a speed of blood stream of organization of body is measured.

Thus, in accordance with the present embodiment, the self-emission-type sensor device 10 is located in such a way that an upper surface of the self-emission-type sensor device 10 is in the same level as the contacting surface 2a of the attaching member 2, and the elastic plate 7 covers an upper surface of the self-emission-type sensor device 10 and the contacting surface 2a of the attaching member 2. Therefore, at the time of measuring bio-information of the specimen 4, a pressure applied to the specimen 4 by the elastic member 7 becomes small, a pressure on a capillary vessel of body which is the specimen 4 is suppressed, similarly with the above-mentioned first embodiment, and a measuring result of bio-information is stabilized, and it is possible to obtain a good S/N ration.

Further, in accordance with the present embodiment, the self-emission-type sensor device 10 is located in such a way that an upper surface of the self-emission-type sensor device 10 is in the same level as the contacting surface 2a of the attaching member 2, and the elastic plate 7 covers an upper surface of the self-emission-type sensor device 10 and the contacting surface 2a of the containing member 2. Therefore, the elastic plate 7 is held in a horizontal condition, so it is possible to further prevent, in advance, piling-up of impurities such as dust.

The present invention is not limited to the above-mentioned embodiments, and a variety of modifications are possible. For example, although an example of measuring a speed of blood stream has been described in the above-mentioned embodiments, the present invention is not limited to the embodiments. For example, by utilizing the difference in absorbance index between hemoglobin oxidized and reduced hemoglobin, and dependency of wavelength thereof, it is possible to measure oxygen saturation in blood. In this case, an LED may be a light source.

Specifically, a plurality of light with a plurality of different wavelengths is irradiated onto the same part of the specimen 4, and the intensity of each reflected light is measured. At this time, although light is absorbed or reflected by hemoglobin contained in blood of the specimen 4, absorbance index varies in accordance with whether the hemoglobin is hemoglobin oxidized or reduced hemoglobin. Therefore, the intensity of reflected light varies in accordance with a rate of hemoglobin oxidized (i.e., oxygen saturation in blood). Absorbance index of hemoglobin depends on wavelength of light, and absorbance index of each of hemoglobin oxidized and reduced hemoglobin varies in accordance with wavelength of irradiated light. Therefore, the intensities of reflected light are different from each other for a plurality of light irradiated at the same time and having different wavelengths. That is, by using a plurality of light with different wavelengths as irradiating means, oxygen saturation in blood can be measured.

In addition to oxygen saturation in blood, for example, by using a red LED or an infrared LED irradiating continuous spectrum light of 700 to 1100 nm as irradiating means, and conducting a spectroscope analysis of absorbance index based on continuous spectrum light, it is possible to measure a chemical component of body liquid (blood or urine). As a specific object to be analyzed, for example, there are a red blood cell (for example, hematocrit, or hemoglobin), a white blood cell, a blood disk, total protein, total cholesterin, blood sugar, and so on.

Further, as mentioned above, the present invention is widely applicable to a field of so-called medical engineering as a blood-stream sensor apparatus. Specifically, since an apparatus according to the present invention can be so small in size that the apparatus can be always attached, such advantage is utilized. For example, an apparatus is attached to an earphone of a hearing aid, a watch, or the like to monitor a health condition of old person, and an apparatus is attached to a toilet seat to measure a stream of blood, and therefore, an apparatus is applicable to health care.

In a field other than medical care, an apparatus according to the present invention is applicable to a household electrical appliance, or a mobile device. For example, by installing an apparatus in a device such as a musical headphone or a headset, or installing an apparatus in a controller of game machine, it is possible to have a function of, for example, predicting a mental state of s user, and automatically selecting music in conformity with his mental state, or changing contents of game. Further, for example, by mounting an apparatus according to the present invention on a steering wheel, a headrest, or the like of an automobile, and monitoring a condition of a driver or a fellow passenger, the present invention is applicable to, for example, the collection of data for assisting a safety driving such as prevention of sleepiness.

Further, the present invention is not confined to the above-mentioned embodiments. Each of the embodiments is an example, and any modification which has the same configurations and produces the same effects as a technical idea in the claims falls in a technical scope of the present invention.

The invention claimed is:

1. A bio-information measuring apparatus in which a self-emission-type sensor device for optically measuring bio-information of specimen is attached to an attaching member,
    wherein the attaching member is composed of elastic material, and is brought into contact with the specimen at the time of measuring the bio-information,
    a hollow is formed in the attaching member, and the self-emission-type sensor device is contained in the hollow, and
    a slanted slope is formed at an inner edge of an aperture of the hollow of the attaching member containing the self-emission-type sensor device with the diameter of the aperture decreased toward the self-emission type sensor device.

2. A bio-information measuring apparatus according to claim 1,
    wherein the self-emission-type sensor device comprises:
    a holding member,
    an irradiating unit located in the holding member which irradiates light onto the specimen, and
    a light-receiving unit located in the holding member which detecting light from the specimen based on the irradiated light, and
    wherein a front surface plate is located in front of the irradiating unit and the light-receiving unit and in an opposed relationship with the specimen, and
    the light is irradiated and received through the front surface plate.

3. An bio-information measuring apparatus according to claim 1,
    wherein a distance between a center of the irradiating unit and a center of the light receiving unit is d, a minimum width of aperture of the hollow is W, and W is greater than d.

4. A bio-information measuring apparatus in which a self-emission-type sensor device for optically measuring bio-information of specimen is attached to an attaching member,
    wherein a hollow is formed in the attaching member, the self-emission-type sensor device is contained in the hollow, and an elastic member of permeability is mounted on at least an upper surface of the self-emission-type sensor device,
    the self-emission-type sensor device is located in such a way that an upper surface of the elastic member of permeability is in the same level as an upper surface of the attaching member, and
    another elastic member of permeability covers an upper surface of the elastic member of permeability and an upper surface of the attaching member.

5. An bio-information measuring apparatus in which a self-emission-type sensor device for optically measuring bio-information of specimen is attached to an attaching member,
    wherein a hollow is formed in the attaching member, the self-emission-type sensor device is contained in the hollow, and a member of permeability is mounted on at least an upper surface of self-emission-type sensor device,
    wherein the self-emission-type sensor device comprises:
    a holding member,
    an irradiating unit located in the holding member which irradiates light onto the specimen, and
    a light receiving unit located in the holding member which detects light from the specimen based on the irradiated light, and
    wherein a distance between a center of the irradiating unit and a center of the light receiving unit is d, a minimum width of aperture of the hollow is W, and W is greater than d, and
    wherein the member of permeability is located in such a way that an upper surface of the member of permeability is slightly lower than an upper surface of the attaching member.

\* \* \* \* \*